(12) United States Patent
Wilhelm

(10) Patent No.: US 12,257,390 B2
(45) Date of Patent: Mar. 25, 2025

(54) MASK ADAPTER FOR CONNECTING TWO BREATHING TUBES OF A CLOSED-CIRCUIT RESPIRATOR TO A BREATHING MASK

(71) Applicant: Dräger Safety AG & Co. KGaA, Lübeck (DE)

(72) Inventor: Christian Wilhelm, Lübeck (DE)

(73) Assignee: DRÄGER SAFETY AG & CO. KGA, Lübeck (DE)

( * ) Notice: Subject to any disclaimer, the term of this patent is extended or adjusted under 35 U.S.C. 154(b) by 553 days.

(21) Appl. No.: 16/225,482

(22) Filed: Dec. 19, 2018

(65) Prior Publication Data

US 2019/0192805 A1 Jun. 27, 2019

(30) Foreign Application Priority Data

Dec. 21, 2017 (DE) .............................. 102017011909

(51) Int. Cl.
| | |
|---|---|
| *A61M 16/08* | (2006.01) |
| *A61M 16/00* | (2006.01) |
| *A61M 16/06* | (2006.01) |
| *A62B 9/04* | (2006.01) |
| *A62B 18/08* | (2006.01) |

(52) U.S. Cl.
CPC .... *A61M 16/0875* (2013.01); *A61M 16/0605* (2014.02); *A61M 16/0833* (2014.02); *A62B 9/04* (2013.01); *A61M 16/0057* (2013.01); *A62B 18/08* (2013.01)

(58) Field of Classification Search
CPC ........ A61M 16/00; A61M 16/08–0891; A61M 16/06–0605; A61M 16/0057; A62B 9/00; A62B 9/04; A62B 18/08; F16L 9/19–20; F16L 41/00; F16L 41/004; F16L 41/023
USPC ............................... 285/131.1; 403/169–161
See application file for complete search history.

(56) References Cited

U.S. PATENT DOCUMENTS

| | | | |
|---|---|---|---|
| 2,486,427 A | 11/1949 | Miller et al. | |
| 3,556,097 A | 1/1971 | Wallace | |
| 3,814,091 A * | 6/1974 | Henkin | ............... A61M 16/104 |
| | | | 128/205.28 |
| 4,534,344 A | 8/1985 | Constance-Hughes | |

(Continued)

FOREIGN PATENT DOCUMENTS

| | | |
|---|---|---|
| CN | 2194187 Y | 4/1995 |
| CN | 101001672 A | 7/2007 |

(Continued)

*Primary Examiner* — Rachel T Sippel
*Assistant Examiner* — Jacqueline M Pinderski
(74) *Attorney, Agent, or Firm* — McGlew and Tuttle, P.C.

(57) ABSTRACT

A mask adapter (10), for connecting two breathing tubes (210) of a closed-circuit respirator (300) to a breathing mask (400), includes a mask connection (20) for a fluid-communicating connection to a breathing area (410) of the breathing mask (400) and two tube connections (30, 40) with tube connection axes (32, 42) for a fluid-communicating connection to a breathing tube (210) each. The first tube connection (30) has an incoming air valve (34) and the second tube connection (40) has an outgoing air valve (44). The first tube connection axis (32) of the first tube connection (30) further forms an acute tube connection angle (β) with the second tube connection axis (42) of the second tube connection (40).

14 Claims, 8 Drawing Sheets

(56) References Cited

U.S. PATENT DOCUMENTS

| | | | | |
|---|---|---|---|---|
| 4,557,261 A * | 12/1985 | Rugheimer | ....... | A61M 16/0833 |
| | | | | 285/317 |
| 4,774,940 A | 10/1988 | Linder | | |
| 4,807,617 A | 2/1989 | Nesti | | |
| 4,827,921 A * | 5/1989 | Rugheimer | ....... | A61M 16/0816 |
| | | | | 128/202.27 |
| 4,852,563 A | 8/1989 | Gross | | |
| 4,955,374 A * | 9/1990 | Pasternack | ............... | A62B 7/10 |
| | | | | 128/207.12 |
| 5,213,096 A * | 5/1993 | Kihlberg | ........... | A61M 16/0833 |
| | | | | 128/205.12 |
| 5,482,031 A * | 1/1996 | Lambert | ........... | A61M 16/1045 |
| | | | | 128/203.26 |
| 5,944,054 A * | 8/1999 | Saieva | ................ | F16K 11/0712 |
| | | | | 128/204.26 |
| 6,209,539 B1 * | 4/2001 | Loescher | .......... | A61M 16/0858 |
| | | | | 128/204.17 |
| 6,578,571 B1 * | 6/2003 | Watt | .................. | A61M 15/0016 |
| | | | | 128/200.14 |
| 2003/0116963 A1 | 6/2003 | Teuscher et al. | | |
| 2005/0186022 A1 | 8/2005 | Garraffa | | |
| 2007/0277828 A1 * | 12/2007 | Ho | ........................ | A61M 16/08 |
| | | | | 128/206.21 |
| 2008/0264413 A1 * | 10/2008 | Doherty | ............ | A61M 16/0825 |
| | | | | 128/202.27 |
| 2009/0021006 A1 | 1/2009 | Hobbs | | |
| 2010/0071688 A1 * | 3/2010 | Dwyer | .............. | A61M 15/0025 |
| | | | | 128/200.18 |
| 2010/0071695 A1 * | 3/2010 | Thiessen | ........... | A61M 16/0833 |
| | | | | 128/204.18 |
| 2010/0229861 A1 * | 9/2010 | Nashed | .................. | A61M 16/00 |
| | | | | 128/203.29 |
| 2012/0285452 A1 * | 11/2012 | Amirav | ............. | A61M 16/0816 |
| | | | | 128/203.29 |
| 2014/0338670 A1 | 11/2014 | Robey et al. | | |
| 2015/0021909 A1 * | 1/2015 | Gulliver | ............. | A61M 39/1011 |
| | | | | 285/319 |
| 2015/0083121 A1 * | 3/2015 | Fisher | ................ | A61M 16/0057 |
| | | | | 128/205.13 |
| 2015/0352310 A1 * | 12/2015 | Martin | .............. | A61M 16/0858 |
| | | | | 128/202.27 |
| 2016/0166794 A1 | 6/2016 | Ratner | | |
| 2017/0232220 A1 | 8/2017 | Huerta | | |
| 2018/0140874 A1 * | 5/2018 | Schuler | .................... | A62B 7/08 |

FOREIGN PATENT DOCUMENTS

| | | |
|---|---|---|
| CN | 101927050 A | 12/2010 |
| CN | 202105344 U | 1/2012 |
| CN | 102847215 A | 1/2013 |
| CN | 103041523 A | 4/2013 |
| CN | 205994909 U | 3/2017 |
| DE | 250364 C | 8/1912 |
| DE | 3823383 A1 | 1/1990 |
| DE | 10 2012 004 359 A1 | 9/2012 |
| EP | 0462412 A2 | 6/1990 |
| EP | 1027905 A2 | 8/2000 |
| EP | 1486233 A1 | 12/2004 |
| EP | 2724743 A1 | 4/2014 |
| FR | 2720949 A3 | 12/1995 |
| IN | 2684868 Y | 3/2005 |
| KR | 20130006602 U | 11/2013 |
| WO | 2013/089714 A1 | 6/2013 |
| WO | 2015038013 A1 | 3/2015 |

* cited by examiner

MASK ADAPTER FOR CONNECTING TWO BREATHING TUBES OF A CLOSED-CIRCUIT RESPIRATOR TO A BREATHING MASK

CROSS REFERENCE TO RELATED APPLICATIONS

This application claims the benefit of priority under 35 U.S.C. § 119 of German Application 10 2017 011 909.0, filed Dec. 21, 2017, the entire contents of which are incorporated herein by reference.

TECHNICAL FIELD

The present invention pertains to a mask adapter for connecting two breathing tubes of a closed-circuit respirator to a breathing mask, to a housing adapter for connecting a breathing tube to such a closed-circuit respirator, to a breathing tube system with two breathing tubes as well as to such a mask adapter and to a process for adapting a breathing tube system to alternative use positions.

BACKGROUND

It is known that closed-circuit respirators are used to protect the users of such protective devices in adverse environments. The closed-circuit respirators are equipped for this with respirator components, which are divided especially into a cooling component, a cleaning component for the outgoing air from the user as well as into a storage component for making oxygen or fresh air available. These closed-circuit respirators are equipped in the prior-art solutions with breathing tube systems, which have essentially two breathing tubes. One is, on the one hand, a first breathing tube for the incoming air and, on the other hand, another one is a second breathing tube for the outgoing air from the user back into the closed-circuit respirator. The two breathing tubes are guided each over a shoulder of the user of the closed-circuit respirator. Some practice is needed for putting on a closed-circuit respirator in the case of the prior-art solutions. Unlike in the case of a heavy backpack, the closed-circuit respirator cannot be put on from the side, but it must be put on over the head. In other words, the closed-circuit respirator together with the breathing tube system is placed on the back over the head of the user, so that the first breathing tube is guided automatically over the left shoulder of the user and the second breathing tube over the right shoulder of the user. The closed-circuit respirator is removed in the reverse order.

The drawback of the prior-art solutions is especially the fixed arrangement of the breathing tubes over the two shoulders. In addition to the fact that a closed-circuit respirator must be put on and removed in a relatively complicated manner, this leads to limited uses. This includes, on the one hand, the drawback that the user cannot remove the closed-circuit respirator simply and rapidly and above all by himself/herself if no sufficient space is available for movements, because this is prevented by the breathing tubes being guided over the two shoulders. Another drawback is that the closed-circuit respirator according to the prior-art solutions can be operated only on the back of the user due to the breathing tubes being guided in a fixed manner over the two shoulders. However, the driving of a vehicle requires the back of a user to remain free. However, a prior-art closed-circuit respirator cannot be placed next to the user while he/she is driving a vehicle, because this would imply the risk that restrictedly guided breathing tubes would be kinked or damaged. In summary, it can consequently be stated that prior-art respirators are fixed to an unambiguous use position and flexibility is thus limited during the use of such closed-circuit respirators.

SUMMARY OF THE INVENTION

An object of the present invention is to at least partially eliminate the above-described drawbacks. In particular, the object of the present invention is to improve the flexibility during the use of a closed-circuit respirator in a cost-effective and simple manner.

The above object is accomplished by a mask adapter according to the invention, by a housing adapter according to the invention, by a breathing tube system according to the invention, as well as by a process according to the invention. Features and details that are explained in connection with the mask adapter according to the present invention also apply, of course, in connection with the housing adapter according to the present invention, with the breathing tube system according to the present invention as well as with the process according to the present invention and vice versa, so that reference is and can always mutually be made to the individual aspects of the present invention concerning the disclosure.

A mask adapter is provided according to the present invention for connecting two breathing tubes of a closed-circuit respirator to a breathing mask. The mask adapter has for this purpose a mask connection for a fluid-communicating connection to a breathing area of the breathing mask. Moreover, the mask adapter is equipped with two tube connections with a tube connection axis each for a fluid-communicating connection to a breathing tube each. The first tube connection has an incoming air valve and the second tube connection has an outgoing air valve. Further, the first tube connection axis of the first tube connection forms an acute tube connection angle with the second tube connection axis of the second tube connection.

A mask adapter according to the present invention is based basically on the technical applications as they are already used for the connection in case of prior-art breathing tube systems. The mask connection is configured for this especially as a quick release fastener in order to be connected to a breathing mask of a user in a fluid-communicating and sealed manner. This is the mask connection, which makes possible the fluid communication, i.e., the inhalation and exhalation in the breathing area of the breathing mask for the user, i.e., the person wearing the breathing mask.

In addition, the combination of two breathing tubes, which likewise open in the mask adapter, is necessary now for feeding the incoming air and removing the outgoing air. The mask adapter has the two tube connections for this, which are configured for a fluid-communicating and sealing connection of the two breathing tubes. The connections described are especially sealed connections, which can provide the fluid-communicating connection in a fluid-tight manner by means of, for example, union nuts or other mechanical securing systems, for example, tube clamps.

A central idea of the present invention is that a defined orientation of the two tube connections is present in the mask adapter. While prior-art solutions usually provide a T-shaped mouthpiece as a mask adapter, an improved orientation of the tube connection axes is provided in the configuration of the mask adapter according to the present invention. In the prior-art T-shaped mouthpieces according to the state of the art, this leads to the tube connections being oriented outwardly left and right at such a T-piece. The correspondingly connected breathing tubes are consequently led away from the T-piece left and right and are guided with a short longitudinal extension over the left and right shoulders to the closed-circuit respirator in the known manner.

To increase the flexibility in the carrying position and the wear comfort, the two breathing tubes can be led out in an improved manner in the configuration according to the present invention. This is made possible by the fact that the two tube connection axes form an acute tube connection angle with one another. The tube connection angle configured as an acute angle is preferably smaller than 45°. However, markedly smaller tube connection angles, especially less than 30°, and preferably less than 20° or 25°, are preferred. As will be explained later, the breathing tubes can be guided in an especially compact manner if the tube connection angle is as small as possible, being especially in the range of about 0°, i.e., the two breathing tubes are guided away from the mask adapter downwardly parallel or essentially parallel from the two tube connections. It may be advantageous in this connection if the orientation of the two tube connection axes is opposite or essentially opposite to a mask connection axis of the mask connection.

It is now possible according to the present invention to connect the mask adapter to the breathing mask in the known manner and to form a fluid-communicating connection in this manner. To make it possible to guarantee the feeding and the removal and incoming air and outgoing air, respectively, the two breathing tubes can be led away from the chest of the user downwardly due to the orientation of the two tube connections and of the two tube connection axes according to the present invention. This makes possible the further guiding of the breathing tubes. The already known solution that the two breathing tubes form an arc over the chest of the user to the left and to the right and are guided each over the left shoulder and the right shoulder of the user to the closed-circuit respirator is also conceivable. However, as an alternative to this carrying position, the two breathing tubes may also be guided together over the left shoulder or together over the right shoulder. The consequence of this is that the other shoulder remains free from breathing tubes and the closed-circuit respirator can thus be put on and taken off laterally, as in the case of a heavy backpack. In particular, the closed-circuit respirator can also be operated away from the back of the user in such a carrying position or if the breathing tubes are guided in such a manner. Due to the fact that the breathing tubes are now led out of the mask adapter downwardly, the closed-circuit respirator can now be positioned, for example, on a passenger seat in a motor vehicle next to the user without kinking and without the risk of damage to the breathing tubes. Not only the wear comfort, the comfort with which putting on and removal can be carried out, but also the flexibility of different intended uses of the closed-circuit respirator is improved by means of a mask adapter according to the present invention.

Last but not least, the breathing tubes guided downward through the mask adapter may be are introduced into the closed-circuit respirator under the arms of the user laterally rearwardly on one side or on both sides rather then being guided over the shoulders of the user.

It should also be pointed out that depending on the positioning of the breathing tubes, the closed-circuit respirator may, of course, be adapted to corresponding inlet positions or adapter interfaces for receiving the correspondingly guided breathing tubes. It is, however, also conceivable that adapter pieces to be described later, for example, the housing adapter, are used to adapt two standard interfaces for the connection of breathing tubes at the closed-circuit respirator to different tube guiding systems or tube guiding directions. This makes it possible to use a closed-circuit respirator having the standard equipment with a mask adapter according to the present invention in many different manners or in different carrying and use positions.

It may be advantageous if the first tube connection axis and the second tube connection axis are oriented parallel or essentially parallel in a mask adapter according to the present invention, so that the tube connection angle is 0° or essentially 0°. It should be pointed out here, in particular, that this is the configuration that is quite different from a parallel coaxial orientation of the two tube connection axes in the prior-art T-shaped mask adapters. A T-shaped mask adapter, which makes the tube connection available to the left and to the right in the prior-art solutions, would have a tube connection angle of about 180° in the sense of the present invention. The configuration with parallel orientation downward with a tube connection angle of 0° or essentially 0° reduces the space requirement even further and increases the compactness of the overall system. Guiding the tubes parallel and in this manner in a space-saving manner makes it possible to achieve the advantages described in the present invention even more easily and better. It is, of course, also conceivable in case of a parallel guiding of the breathing tubes that these are then connected to one another and may form quasi a connected double tube system or a double breathing tube.

It may likewise be advantageous if the mask connection has a mask connection axis in a mask adapter according to the present invention, and the tube connection axes are configured axially symmetrically to the mask connection axis. In particular, the axially symmetrical configuration is symmetrical to a plane of division of the mask, which extends through the center of the breathing mask and contains the mask connection or the mask connection axis. An overall symmetry is thus obtained for the mask, which symmetry has an advantageous effect especially concerning the tensile forces, which are transmitted by the breathing tubes to the breathing mask during the movement of the user. A symmetrical load distribution causes the pulling or the transmission of the tensile load on the breathing mask to be predictable and thus tolerable for the user in a comfortable manner.

Further advantages can be achieved if the first tube connection axis is adjustable relative to the second tube connection axis for a change in the tube connection angle in a mask adapter according to the present invention. The orientation of the tube connection in relation to one another may be relatively adjustable, for example, tiltable. An individual tube connection or even both tube connections may have this relative adjustability, so that adaptation to the particular manner of wearing is possible in a more flexible manner, and adaptation or a variation according to the personal preference of the user of the closed-circuit respirator may also be provided in this manner. It is preferable if the change in the tube connection angle is limited to the range of acute tube connection angles, so that the adaptability does not have to be needlessly wide in order not to compromise the compactness of the mask adapter as a component despite an increased flexibility. To make it possible to set correspondingly changed angular positions of the tube connection angle, it may be advantageous if corresponding locking devices define and fix individual angular positions.

It may likewise be advantageous if the mask connection in a mask adapter according to the present invention has a mask connection interface, which is free from rotation in at least some sections, for connection to the breathing mask, which connection is relatively rotatable in at least some sections. This quasi leads to an additional degree of freedom, which allows a pendular motion of the mask adapter in front of the user's breathing mask. This expanded degree of freedom leads to improved comfort or improved sensation during wear and increases the flexibility and the mobility of the user, especially of the user's head.

It may likewise be advantageous if the first tube connection and the second tube connection are arranged in a mask adapter according to the present invention next to one another at the same level, and especially the first tube connection and the second tube connection are arranged in a common plane or essentially in a common plane. This leads to a marked improvement in the compactness of the mask adapter and the possibility of mounting is facilitated as well. The entire mask adapter thus becomes small and lightweight and is optimized in terms of both the possibility of mounting and a nuisance factor in front of the chest or in front of the neck area of the user.

The present invention also pertains to a housing adapter for connecting a breathing tube to a closed-circuit respirator. Such a housing adapter has a housing connection with a housing connection axis for a fluid-communicating connection to a respirator component of the closed-circuit respirator. Further, the housing adapter is equipped with an angle connection to an angle connection axis for a fluid-communicating connection to the breathing tube. The housing connection axis forms a housing connection angle of less than 160° with the angle connection axis. A housing adapter is used especially in combination with a mask adapter according to the present invention. In case of the standard, upwardly directed outlet directions of the corresponding opposite connections of a closed-circuit respirator, the housing adapter makes it possible to vary the guiding of the breathing tube. Due to the fact that the housing adapter now makes it possible quasi as an elbow to bend the outlet direction from the respirator component of the closed-circuit respirator from, it is possible to improve the branching off of the breathing tubes both to the side and to the front. In particular, a carrying position as it was explained, with the breathing tubes on a single shoulder of the user, so that the second shoulder of the user remains free, is improved further with a housing adapter according to the present invention. In particular, the compactness with which the breathing tubes are guided is improved and the absence of kinks is optimized at the same time. The risk of kinking or damage due to a correspondingly stressed guiding of the breathing tubes can be effectively reduced by the housing adapter. The housing connection angle is preferably lower now then 160° and is preferably in the range of about 90°+20°. A housing adapter according to the present invention thus likewise improves the flexibility, as this was already explained with reference to a mask adapter according to the present invention, so that the same advantages that were explained in detail with reference to a mask adapter according to the present invention are also achieved by the housing adapter.

A housing adapter according to the present invention can be perfected such that the housing connection is arranged at a first adapter component and the angle connection at a second adapter component, which are connected to one another. This leads to an especially simple embodiment, because it is also possible, in particular, to combine different materials with one another for the two connections. For example, a connection of the two adapter components can thus be established even by a two-component injection molding process. Bonding or locking of the individual adapter components to one another may also be provided. Plug-type or screw connections as well as clamped connections may, of course, also be provided within the framework of the present invention for the connection of the two adapter components.

A further advantage can be achieved if the housing connection is formed in a housing adapter from an elastic material, especially one containing an elastomeric material. The increased flexibility due to the elastic configuration of the material damps, on the one hand, relative motions of the breathing tubes in relation to the user. Moreover, this leads, in combination with the two components, to the possibility of providing a stable connection of the breathing tubes to the closed-circuit respirator in a simple and cost-effective manner.

It may likewise be advantageous if the angle connection is configured with a reversible fastening device in a housing adapter according to the present invention. A reversible fastening makes it possible, especially rapidly and simply, for example, in the form of a quick release fastener, to mount the housing adapter on the breathing tube or to remove it from same. For a rapid variation before the beginning of the use, the user can now decide rapidly, simply and above all in a short time which carrying position is necessary or ideal for the imminent use.

Moreover, it is advantageous if the angle connection axis is adjustable relative to the housing connection axis in a housing adapter according to the present invention for changing the housing connection angle. An additional degree of freedom, which makes possible a corresponding switchover between different carrying positions of the breathing tubes, can be made available here as well. To make it possible to reach or define the corresponding end positions or switching positions better, these end positions or use positions may be fixed mechanically as locking positions by a locking device.

The present invention also pertains to a breathing tube system for connection to a closed-circuit respirator, having a mask adapter according to the present invention. A breathing tube is connected to each tube connection of the mask adapter in a fluid-communicating manner. The fluid-communicating connection may be made available, for example, by means of seals or sealants or by means of mechanical fixing components, for example, union nuts. Due to the use of a mask adapter according to the present invention, a breathing tube system according to the present invention offers the same advantages as those explained in detail with reference to the mask adapter according to the present invention.

It is also possible that exactly one breathing tube is connected in a breathing tube system according to the present invention at the opposite end to the tube connection with a housing adapter according to the present invention in a fluid-communicating manner. Thus, such a breathing tube system leads, moreover, to the advantages that were explained in detail with reference to the housing adapter according to the present invention. If exactly one breathing tube is equipped with the housing adapter, the other breathing tube is free from such a housing adapter, so that it is possible to distribute the two breathing tubes, which are guided together over the shoulder of the user, on the back of the user to the respirator components of the closed-circuit respirator in a simple and cost-effective manner.

The present invention also pertains to a process for adapting a breathing tube system according to the present invention to an alternative carrying position, having the following step: Establishment of a fluid-communicating connection between the end of exactly one breathing tube, which end is located opposite the tube connection, with a housing adapter according to the present invention.

A breathing tube system is thus prepared according to the above process, so that quasi a simple and cost-effective switchover becomes possible between different carrying variants by means of a process according to the present invention.

Further advantages, features and details of the present invention appear from the following description, in which exemplary embodiments of the present invention are described in detail with reference to the drawings. The features mentioned in the claims and in the description may be essential for the present invention both individually or in any desired combination. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 2:
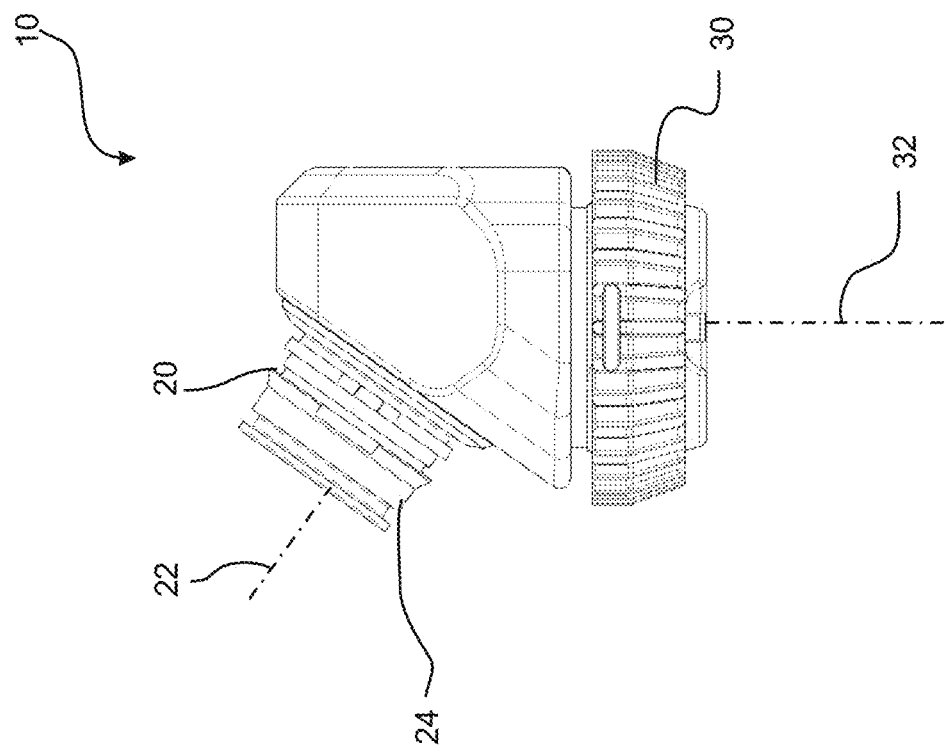
FIG. 2 is a lateral view showing the embodiment of FIG. 1.
Figure 1:
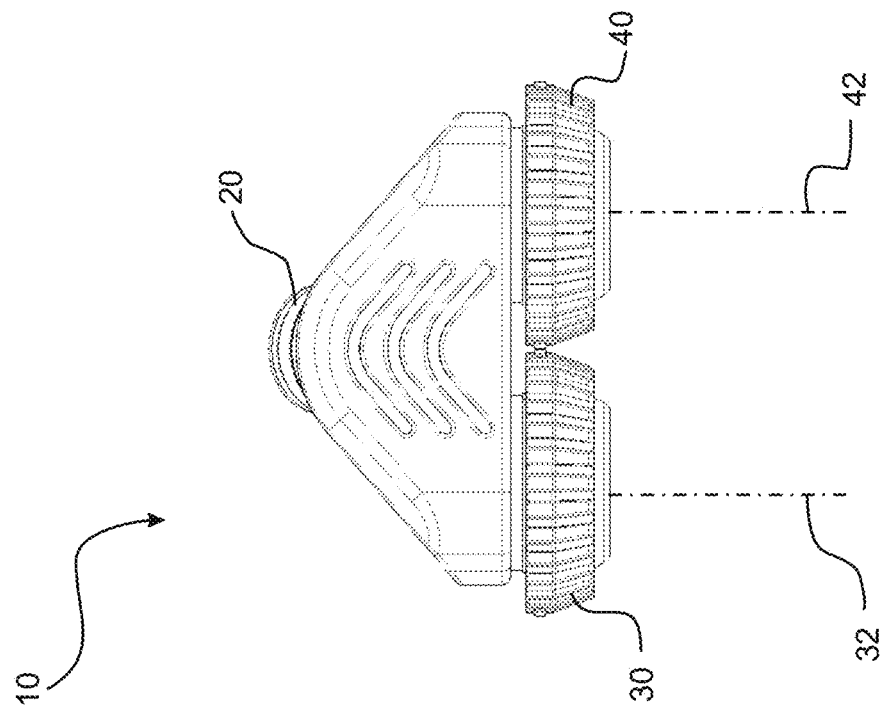
FIG. 1 is a front view showing an embodiment of a mask adapter according to the present invention.

Referring to the drawings, FIGS. 1 through 4 show a mask adapter 10 according to the present invention. This is equipped with a mask connection 20, which can provide a fluid-communicating connection to a breathing mask 400 along a mask connection axis 22. A corresponding connection is shown in FIG. 5. There is a fluid-communicating connection according to FIG. 5 to the breathing area 410 in the interior of the breathing mask 400 via a mask connection interface 24, which has especially a rotation-free configuration. This can be established, for example, by a quarter-turn fastener, locking in or by the use of union nuts in the known manner.

This mask adapter 10 according to FIGS. 1 through 5 is equipped according to the present invention with a first tube connection 30 and with a second tube connection 40. Each of these tube connections has a tube connection axis 32 and 42, respectively, which are oriented at right angles downwardly and hence parallel to one another in the embodiment according to FIGS. 1 through 5. The tube connection angle α set thereby is correspondingly in the range of 0° and has a configuration contrary to prior-art solutions, in which the tube connections are oriented to the left and to the right in case of T-shaped mouth fittings. The mask adapter 10 includes a mask adapter body 4, an upper end portion 5, a lower end portion 6, an angled mask adapter body surface 7, another mask adapter body surface 8 and a mask adapter body longitudinal axis 9.

Figure 4:
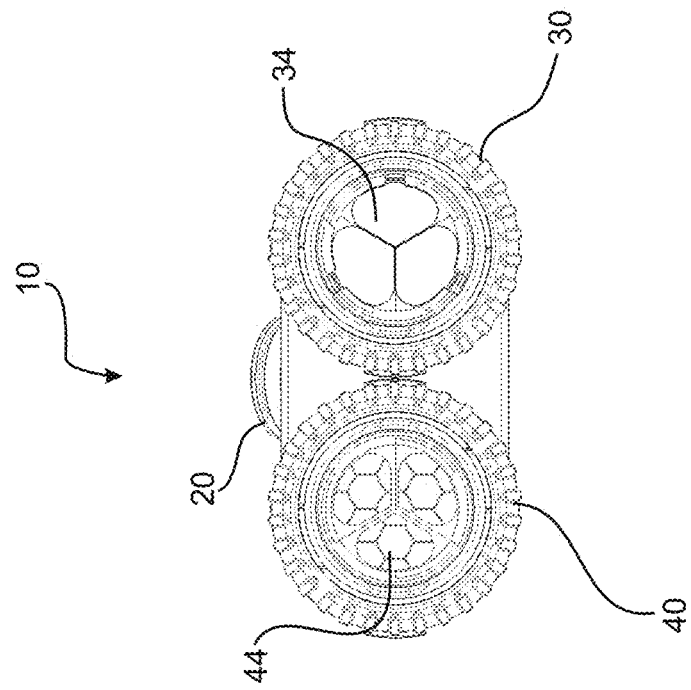
FIG. 4 is a bottom view showing the embodiment according to FIGS. 1 through 3.
Figure 3:
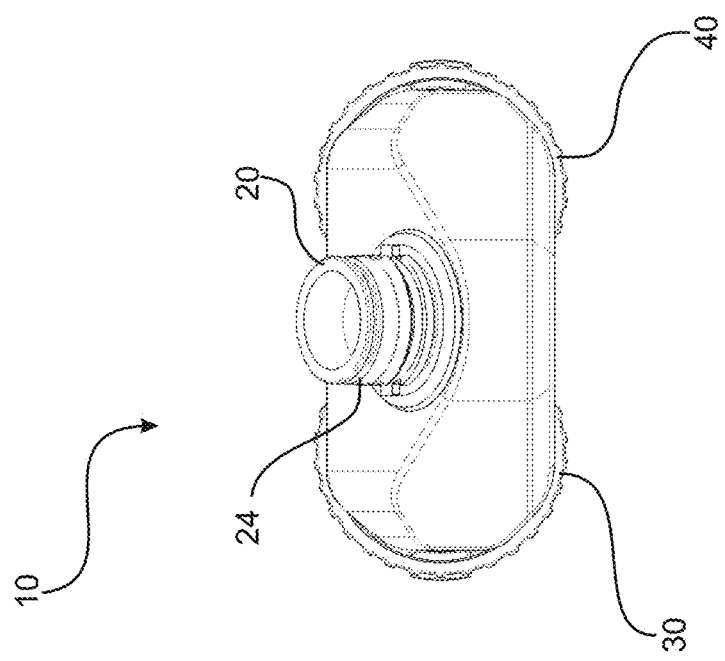
FIG. 3 is a top view showing the embodiment according to FIGS. 1 and 2.
Figure 5:
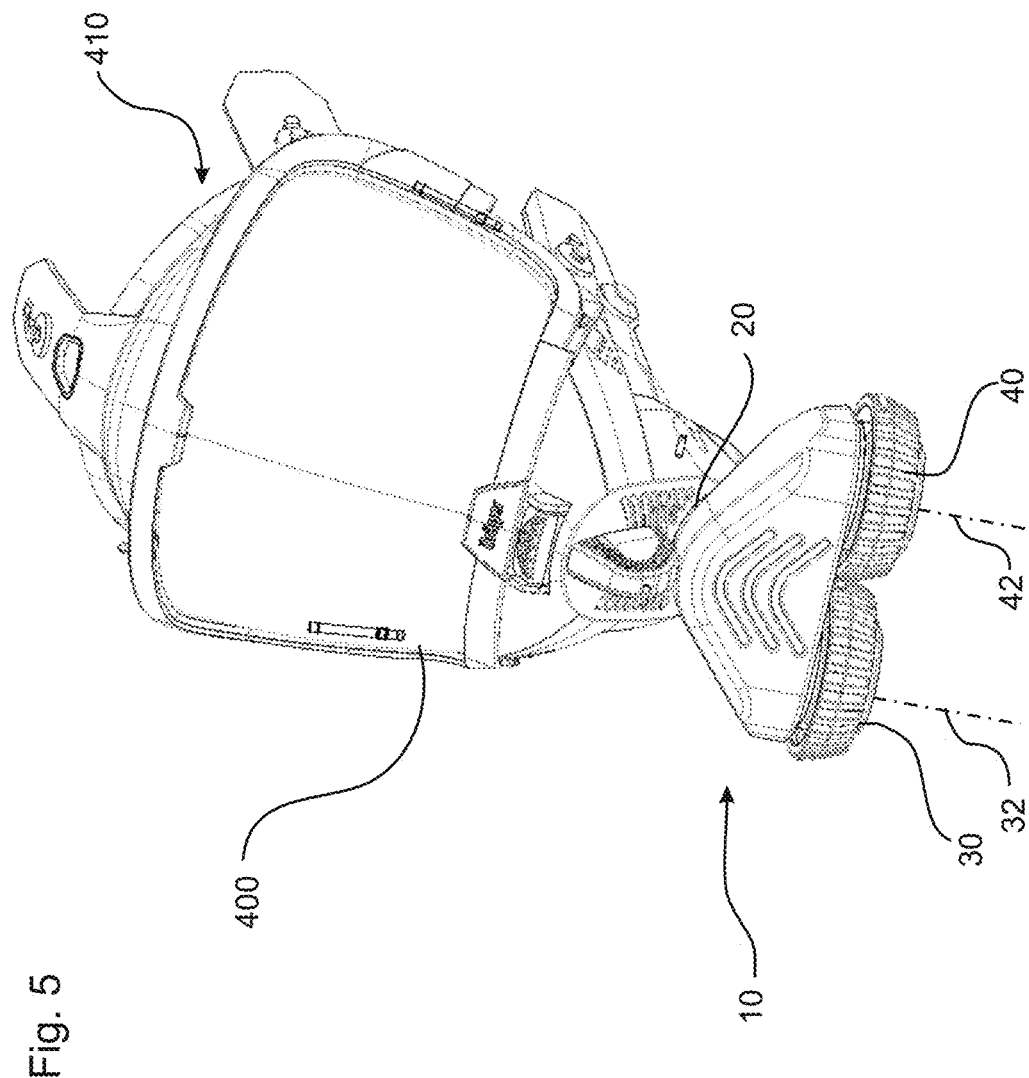
FIG. 5 is a perspective view showing the embodiments according to FIGS. 1 through 4 at a breathing mask.

To also distinguish the two tube connections 30 and 40 according to whether they carry incoming air and outgoing air, the bottom view in FIG. 4 shows that an incoming air valve 34 is arranged in the first tube connection 30 and an outgoing air valve 44 is arranged in the second tube connection 40.

Figure 6:
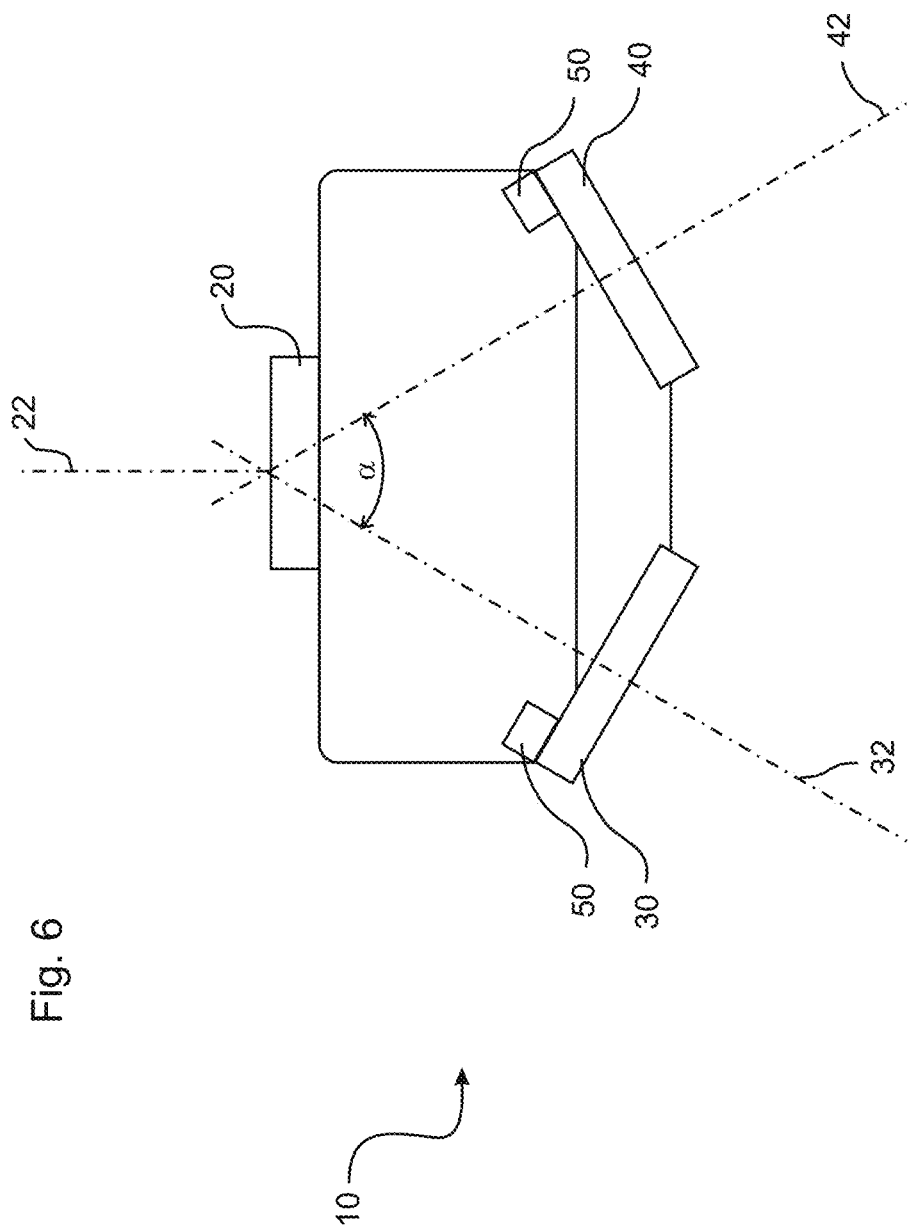
FIG. 6 is a schematic view showing another embodiment of a mask adapter according to the present invention.
Figure 7:
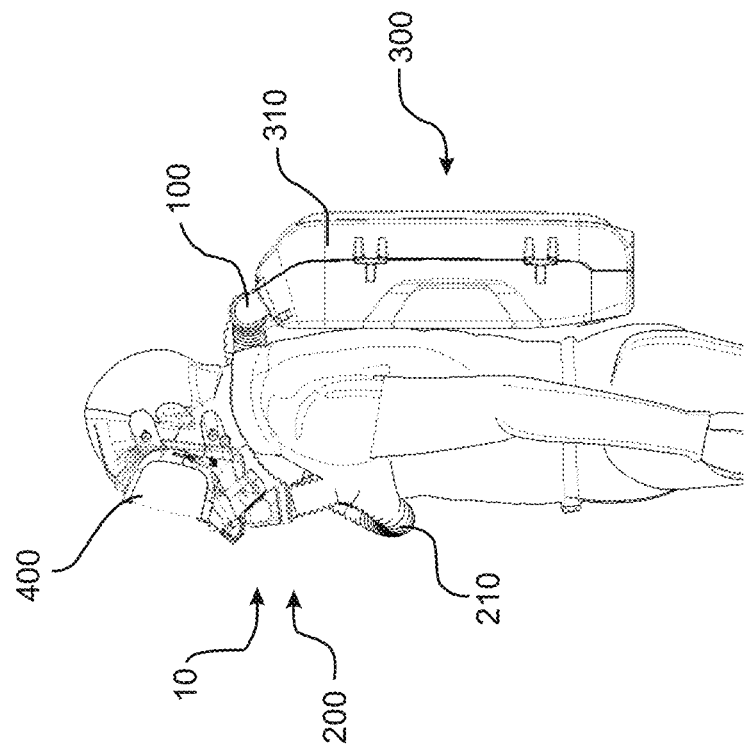
FIG. 7 is a front view showing the embodiments according to FIGS. 1 through 5 at a user.
Figure 8:
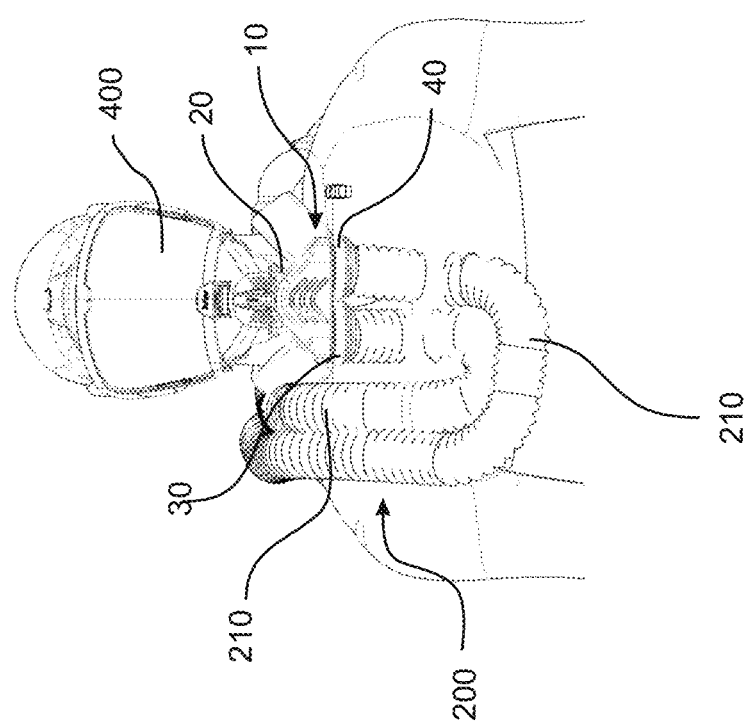
FIG. 8 is a lateral view showing the embodiment according to FIG. 7.
Figure 9:
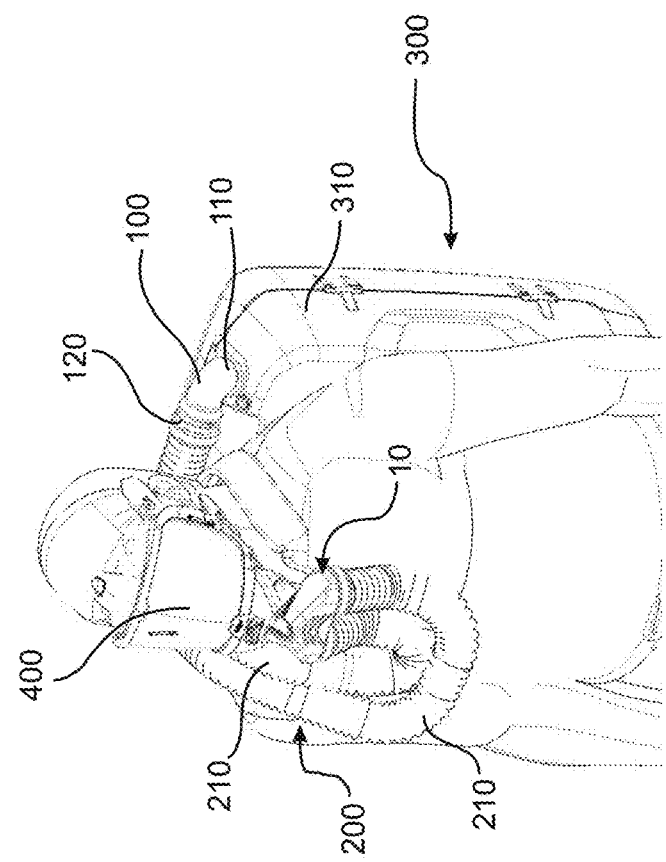
FIG. 9 is a top view showing the embodiments according to FIGS. 7 and 8.
Figure 10:
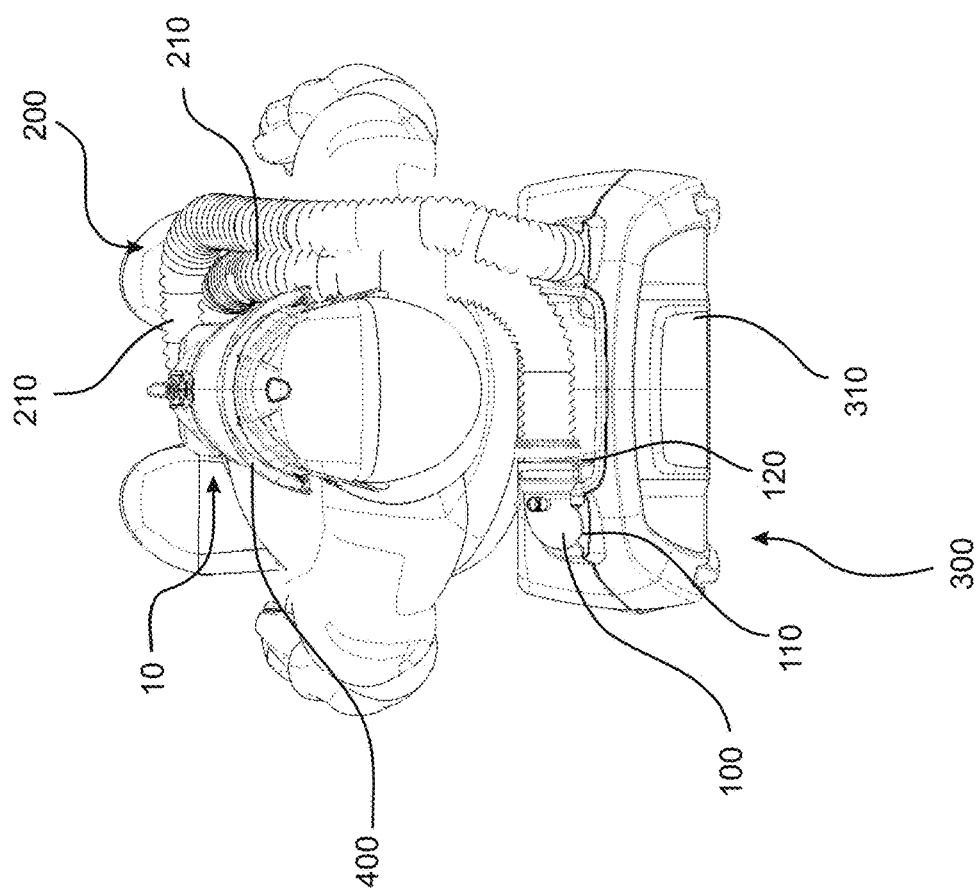
FIG. 10 is an isometric view showing the embodiments according to FIGS. 7 through 9.

FIG. 6 shows an alternative embodiment of the mask adapter 10. The two tube connections 30 and 40 are oriented here differently, so that an acute angle α in the range of about 30° is formed now between the first tube connection axis 32 and the second tube connection axis 42. The first tube connection axis 32 may be adjusted relative to the second tube connection axis 42 for changing the tube connection angle. This allows the tube connections to be adjustable or tiltable via the locking devices 50, shown in FIG. 6. The angular position of the respective tube connection (30 or 40) is set by the corresponding locking devices 50. As an example, the locking devices 50 each include multiple detents to set multiple different angles of the tube connection. The locking devices 50 may further or alternatively include plug-type connections or clamped connections for different angles. To alter the angle between the tube connections, the locking device 50 may be connected only to one or to both tube connections (30 and/or 40). For example, the locking device 50 may be arranged on or in the tube connection 30 or the locking device 50 is generally coupled to the tube connection 30 for an adjustment of an orientation of the tube connection 30. The angle connection axis is also adjustable relative to the housing connection axis for changing the housing connection angle with the corresponding locking devices 50. Thus, similar to connection with the tube connections 30 and 40, the locking device 50 can be, for example, connected to the housing connection 110 and/or the angle connection 120. The locking device 50 can also include multiple detents, plug-type connections or clamped connections to set different angles of the housing connection or the angle connection.

FIGS. 7 through 10 show schematically how the guiding of the tubes of the breathing tube system 200 can be improved by means of a mask adapter 10 according to FIGS. 1 through 5. Based on the tube connections 30 and 40 of the mask adapter 10, which are oriented parallel downwardly, it can be clearly seen especially in FIG. 7 how the two breathing tubes 210 are guided downwardly parallel to one another centrally in front of the chest of the user. In a common bend, the two breathing tubes 210 of the breathing tube system 200 now run further, guided parallel, over a common right shoulder of the user, so that the left shoulder of the user remains free from the breathing tube system 210. It can be clearly seen in the top view in FIG. 9 and especially also in FIG. 10 how the two breathing tubes 210 are now guided to the two standard interfaces of the closed-circuit respirator 300 on the back side of the user. A plurality of respirator components 310 are arranged in the interior of the closed-circuit respirator 300, and each of the two breathing tubes 210 leads to one of these respirator components 310 each, especially to an outgoing air purification component and to an incoming air cooling component.

As can clearly be seen in FIGS. 7 through 10, the guiding of the tubes is optimized even more in the breathing tube system 200 in this embodiment by the use of a housing adapter 100. Such a housing adapter 100 will be explained in more detail on the basis of FIGS. 11 through 14.

FIGS. 11 through 14 show a housing adapter 100, which is composed of two adapter components 102 and 104 here. The housing adapter 100 is equipped at the first adapter component 102 with a housing connection 110, which is configured for connection to the housing of the closed-circuit respirator 300 or to the respirator component 310. The second adapter component 104 has the angle connection 120 in order make possible a corresponding connection to a breathing tube 210. Mechanical union nuts are again provided here for sealing and fastening. The connection between the two adapter components 102 and 104 may be established both according to a two-component injection molding process and a bonding process or other fastening processes.

Figure 12:
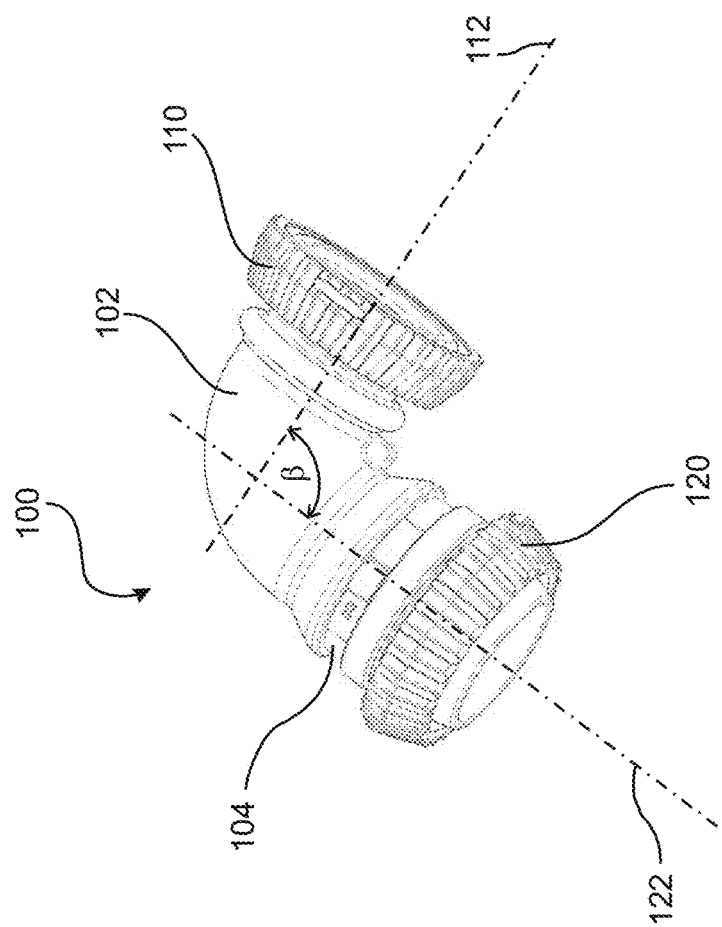
FIG. 12 is a perspective view showing the embodiment according to FIG. 11.
Figure 11:
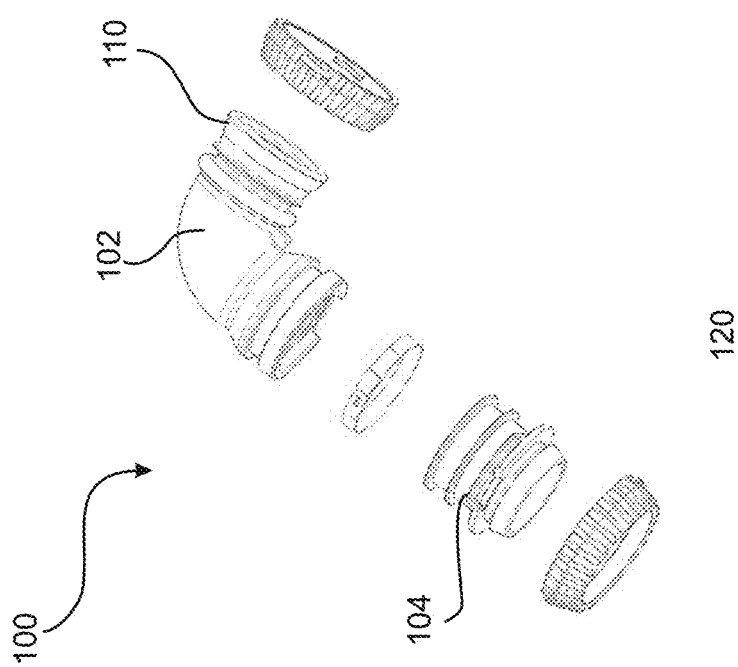
FIG. 11 is an exploded view showing an embodiment of a housing adapter according to the present invention.

The axis ratio of the angle connection 120 and the housing connection 110 can be seen in FIG. 12. The housing connection axis 112 forms a housing connection angle β of about 90° here with the angle connection axis 122. This 90° bend (kink) makes it possible to lead off the second breathing tube 210 laterally along the back of the user, as it can be seen especially in the top view in FIG. 9.

Figure 14:
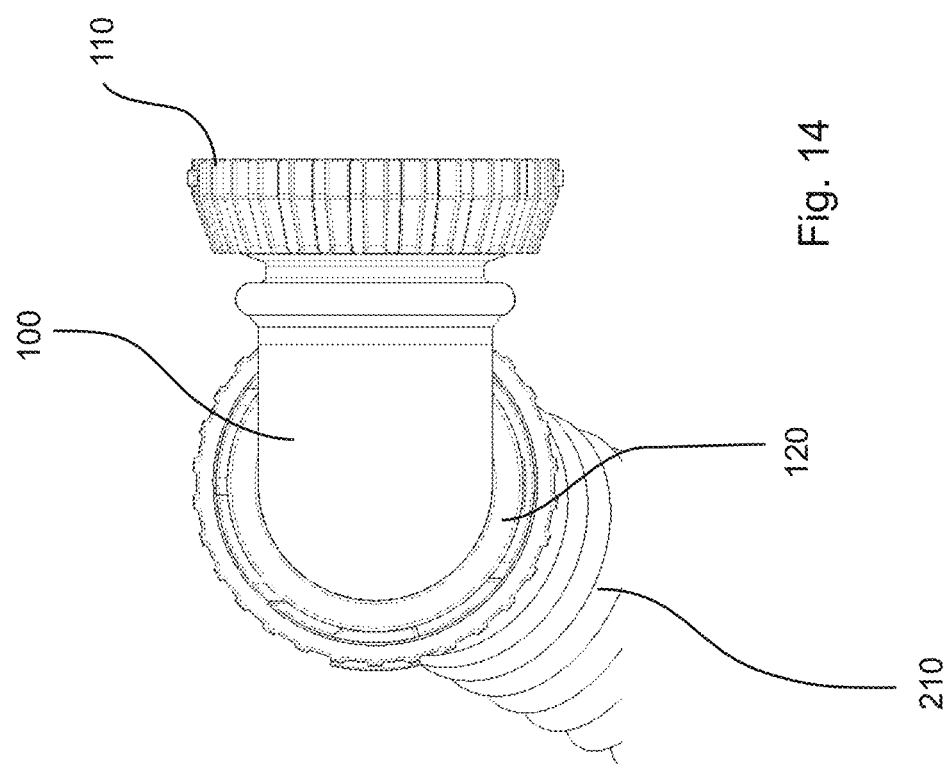
FIG. 14 is a lateral view showing the embodiments according to FIGS. 11 through 13.
Figure 13:
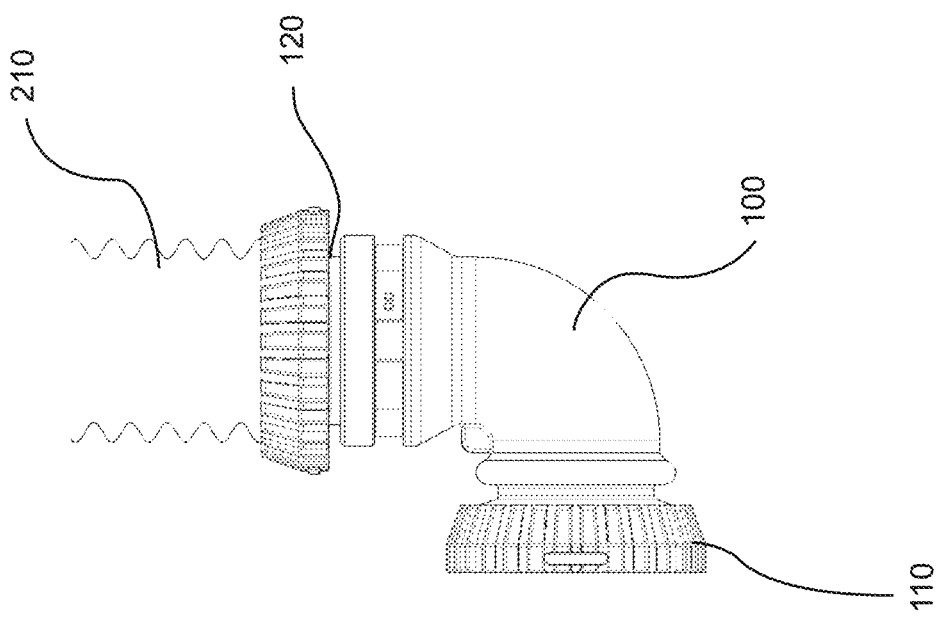
FIG. 13 is a top view showing the embodiment according to FIGS. 11 and 12.

The correlation to the breathing tube 210 is shown in more detail in FIGS. 13 and 14, as it can likewise be seen especially in the arrangement according to FIGS. 7 through 10.

The above explanation of the embodiments describes the present invention exclusively within the framework of examples. Individual features of the embodiments, if technically meaningful, may, of course, be freely combined with one another without going beyond the scope of the present invention.

While specific embodiments of the invention have been shown and described in detail to illustrate the application of the principles of the invention, it will be understood that the invention may be embodied otherwise without departing from such principles.

What is claimed is:

1. A mask adapter for connecting two breathing tubes of a closed-circuit respirator to a breathing mask, the mask adapter comprising:
   a mask connection for a fluid-communicating connection to a breathing area of the breathing mask, the mask connection being configured to be placed adjacent to the breathing mask;
   a first tube connection, with a first tube connection axis, for a fluid-communicating connection to a breathing tube, the first tube connection having an incoming air valve;
   a second tube connection, with a second tube connection axis, for another fluid-communicating connection to another breathing tube, the second connection having an outgoing air valve, wherein the first tube connection axis of the first tube connection forms an acute tube connection angle with the second tube connection axis of the second tube connection, wherein the first tube connection axis is adjustable relative to the second tube connection axis for changing the tube connection angle;
   a mask adapter body comprising an upper end portion, a lower end portion and an angled mask adapter body surface configured to face in a direction of the breathing mask, the angled mask adapter body surface extending from the upper end portion to the lower end portion, the mask adapter body further comprising another mask adapter body surface located opposite the angled mask adapter body surface, the another mask adapter body surface being configured to face in a direction away from the breathing mask, wherein a distance between the angled mask adapter body surface and the another mask adapter body surface increases in a direction from the upper end portion to the lower end portion of the mask adapter body, the mask connection being substantially in a middle area of the angled mask adapter body surface.

2. The mask adapter in accordance with claim 1, wherein the first tube connection axis and the second tube connection axis are independently adjustable to extend in a same direction.

3. The mask adapter in accordance with claim 2, wherein:
   the mask connection has a mask connection axis;
   the first tube connection axis and the second tube connection axis are independently adjustable to be axially symmetrical to the mask connection axis.

4. The mask adapter in accordance with claim 1, wherein the mask adapter body is connected to the mask connection, the first tube connection and the second tube connection, the mask adapter body having a mask adapter body longitudinal axis, the angled mask adapter body surface extending in a direction traversing the mask adapter body longitudinal axis, the angled mask adapter body surface extending between the upper end portion and the lower end portion, the mask adapter body longitudinal axis, the first tube connection axis and the second tube connection axis extending in a same direction, the first tube connection and the second tube connection extending from the lower end portion, the mask connection extending from the angled mask adapter body surface in a mask connection extending direction, the mask connection extending direction being non-parallel to the mask adapter body longitudinal axis, wherein the mask connection comprises a mask connection interface, the mask connection interface being free from rotation relative to the mask adapter, wherein the mask connection interface is connectable to the breathing mask to allow relative rotation between the mask adapter and the breathing mask, at least a portion of the mask connection being configured to be directly adjacent to the breathing mask, the breathing tube extending between the breathing mask and the closed-circuit respirator, the another breathing tube extending between the breathing mask and the closed-circuit respirator, wherein each of the first tube connection axis of the first tube connection and the second tube connection axis of the second tube connection is independently adjustable such that the first tube connection axis and the second tube connection axis are independently adjustable relative to one another for changing a tube connection angle, the another mask adapter body surface being parallel to the mask adapter body longitudinal axis, the upper end portion being axially opposite the lower end portion with respect to the mask adapter body longitudinal axis.

5. The mask adapter in accordance with claim 1, wherein the first tube connection and the second tube connection are configured to be arranged next to each other at an equal level, the first tube connection having a connection plane perpendicular to the first tube connection axis and the second tube connection having a connection plane perpendicular to the second tube connection axis, the connection plane of the first tube connection and the connection plane of the second tube connection being arranged in a common plane or essentially in a common plane.

6. A breathing tube system for connection to a closed-circuit respirator, the breathing tube system comprising:
   a mask adapter comprising an upper end portion, a lower end portion, an angled mask adapter body surface, another mask adapter body surface, a mask connection substantially in a middle area of the angled mask adapter body surface for a fluid-communicating connection to a breathing area of the breathing mask, a first tube connection, with a first tube connection axis, for a fluid-communicating breathing tube connection, the first tube connection having an incoming air valve, and a second tube connection, with a second tube connection axis, for another breathing tube fluid-communicating connection, the second connection having an outgoing air valve, the mask connection being placed adjacent to the breathing mask, wherein the first tube connection axis of the first tube connection forms an acute tube connection angle with the second tube connection axis of the second tube connection, wherein the first tube connection axis is adjustable relative to the second tube connection axis for changing the tube connection angle, the angled mask adapter body surface being configured to face in a direction of the breathing mask, the angled mask adapter body surface extending from the upper end portion to the lower end portion, the another mask adapter body surface being located opposite the angled mask adapter body surface, the another mask adapter body surface being configured to face in a direction away from the breathing mask, wherein a distance between the angled mask adapter body surface and the another mask adapter body surface increases in a direction from the upper end portion to the lower end portion of the mask adapter body;
   a first breathing tube fluidly communicating connected to the first tube connection; and
   a second breathing tube fluidly communicating connected to the second tube connection.

7. The breathing tube system in accordance with claim 6, further comprising a housing adapter, wherein:
   said first breathing tube comprises an opposite fluid communication connection end, opposite to the first tube connection, fluidly communicating connected with the housing adapter; and
   the housing adapter comprises a housing connection with a housing connection axis for a fluid-communicating connection to a respirator component of the closed-circuit respirator, and an angle connection with an angle connection axis for a fluid-communicating connection to the breathing tube, wherein the housing connection axis forms a housing connection angle of less than 160° with the angle connection axis.

8. The breathing tube system in accordance with claim 7, wherein:
   the mask connection has a mask connection axis;
   the first tube connection axis and the second tube connection axis are axially symmetrical to the mask connection axis.

9. The breathing tube system in accordance with claim 7, wherein the angle connection axis is adjustable relative to the housing connection axis for changing the housing connection angle.

10. The breathing tube system in accordance with claim 6, wherein:
   a housing connection is arranged at a first adapter component;
   an angle connection is arranged at a second adapter component; and
   the first adapter component is connected to the second adapter component.

11. The breathing tube system in accordance with claim 10,
   wherein the housing connection is comprised of an elastic material, the mask adapter body being connected to the mask connection, the first tube connection and the second tube connection, the mask adapter body having a mask adapter body longitudinal axis, the angled mask adapter body surface extending in a direction traversing the mask adapter body longitudinal axis, the angled mask adapter body surface extending between the upper end portion and the lower end portion, the mask adapter body longitudinal axis, the first tube connection axis and the second tube connection axis extending in a same direction, the first tube connection and the second tube connection extending from the lower end portion, the mask connection extending from the angled mask adapter body surface in a mask connection direction, the mask connection direction not being parallel to the mask adapter body longitudinal axis, at least a portion of the mask connection being directly adjacent to the breathing mask, wherein each of the first tube connection axis of the first tube connection and the second tube connection axis of the second tube connection is independently adjustable such that the first tube connection axis and the second tube connection axis are independently adjustable relative to one another for changing a tube connection angle, the first breathing tube extending between the breathing mask and the closed-circuit respirator, the second breathing tube extending between the breathing mask and the closed-circuit respirator, the another mask adapter body surface being parallel to the mask adapter body longitudinal axis, the upper end portion being axially opposite the lower end portion with respect to the mask adapter body longitudinal axis.

12. A process for adapting a breathing tube system to an alternative carrying position, the process comprising the step of:
   providing the breathing tube system so as to comprise a mask adapter comprising an angled mask adapter body surface, an upper end portion, a lower end portion, a mask connection substantially in a middle area of the angled mask adapter body surface for a fluid-communicating connection to a breathing area of the breathing mask, a first tube connection, with a first tube connection axis, for a breathing tube fluid-communicating connection, the first tube connection having an incoming air valve, and a second tube connection, with a second tube connection axis, for another breathing tube fluid-communicating connection, the second connection having an outgoing air valve, the mask connection being placed adjacent to the breathing mask, wherein the first tube connection axis of the first tube connection forms an acute tube connection angle with the second tube connection axis of the second tube connection, a first breathing tube fluidly communicating connected to the first tube connection, and a second breathing tube fluidly communicating connected to the second tube connection, wherein the first tube connection axis is adjustable relative to the second tube connection axis for changing the tube connection angle, the angled mask adapter body surface extending from the upper end portion to the lower end portion, the angled mask adapter body surface being configured to face in a direction of the breathing mask, the mask adapter body further comprising another mask adapter body surface located opposite the angled mask adapter body surface, the another mask adapter body surface being configured to face in a direction away from the breathing mask, wherein a distance between the angled mask adapter body surface and the another mask adapter body surface increases in a direction from the upper end portion to the lower end portion of the mask adapter body;

establishing a fluid-communicating connection between an opposite end of said first breathing tube, which opposite end is located opposite the first tube connection, with a housing adapter comprising a housing connection with a housing connection axis for a fluid-communicating connection to a respirator component of the closed-circuit respirator, and an angle connection with an angle connection axis for a fluid-communicating connection to the breathing tube, wherein the housing connection axis forms a housing connection angle of less than 160° with the angle connection axis.

13. The process according to claim 12, wherein:
the mask connection has a mask connection axis;
the first tube connection axis and the second tube connection axis are axially symmetrical to the mask connection axis;
the housing connection is arranged at a first adapter component;
the angle connection is arranged at a second adapter component;
the first adapter component is connected to the second adapter component;
the housing connection is comprised of an elastic material; and
the angle connection axis is adjustable relative to the housing connection axis for changing the housing connection angle.

14. The process in accordance with claim 12, wherein the first tube connection has a connection plane perpendicular to the first tube connection axis and the second tube connection has a connection plane perpendicular to the second tube connection axis, the connection plane of the first tube connection and the connection plane of the second tube connection being arranged in a common plane or essentially in a common plane, the mask adapter further comprising a mask adapter body connected to the mask connection, the mask adapter body comprising the angled mask adapter body surface, the first tube connection and the second tube connection, the mask adapter body having a mask adapter body longitudinal axis, the angled mask adapter body surface extending in a direction traversing the mask adapter body longitudinal axis, the angled mask adapter body surface extending between the upper end portion and the lower end portion, the first tube connection and the second tube connection extending from the lower end portion, the mask connection extending from the angled mask adapter body surface in a mask connection direction, the mask connection direction being non-parallel to the mask adapter body longitudinal axis, at least a portion of the mask connection being located directly adjacent to the breathing mask, wherein each of the first tube connection axis of the first tube connection and the second tube connection axis of the second tube connection is independently adjustable such that the first tube connection axis and the second tube connection axis are adjustable relative to one another for changing a tube connection angle, the tube connection angle being adjustable to form an acute tube connection angle with the second tube connection axis of the second tube connection, the first breathing tube and the second breathing tube extending between the breathing mask and a closed-circuit respirator, the another mask adapter body surface being parallel to the mask adapter body longitudinal axis, the upper end portion being axially opposite the lower end portion with respect to the mask adapter body longitudinal axis.

* * * * *